United States Patent
Karube

(10) Patent No.: US 12,419,569 B2
(45) Date of Patent: Sep. 23, 2025

(54) SWALLOWING EVALUATION SYSTEM AND SWALLOWING EVALUATION METHOD

(71) Applicant: FUJIFILM Corporation, Tokyo (JP)

(72) Inventor: Mikihiko Karube, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 91 days.

(21) Appl. No.: 18/322,393

(22) Filed: May 23, 2023

(65) Prior Publication Data

US 2023/0293091 A1     Sep. 21, 2023

Related U.S. Application Data

(63) Continuation of application No. PCT/JP2021/043235, filed on Nov. 25, 2021.

(30) Foreign Application Priority Data

Nov. 26, 2020 (JP) .................... 2020-195807

(51) Int. Cl.
 *A61B 5/00* (2006.01)
 *A61B 7/00* (2006.01)
 *A61B 8/08* (2006.01)

(52) U.S. Cl.
 CPC .......... *A61B 5/4205* (2013.01); *A61B 5/7267* (2013.01); *A61B 7/003* (2013.01); *A61B 8/085* (2013.01)

(58) Field of Classification Search
 CPC ..... A61B 5/4205; A61B 5/7267; A61B 7/003; A61B 8/085; A61B 8/463; A61B 8/5223; A61B 8/5292
 See application file for complete search history.

(56) References Cited

FOREIGN PATENT DOCUMENTS

| JP | 2010253257 A | * | 11/2010 | ........... A61B 8/4427 |
| JP | 2018000871 A | * | 1/2018 | |
| JP | 2020089613 A | * | 6/2020 | ............... A61B 5/11 |

OTHER PUBLICATIONS

Dudik et al. 2018 BioMed. Eng. OnLine 17: article 69 18 pages (Year: 2018).*
Wakabayashi 2020 J. Gen. Fam. Med. 21:1â2 (Year: 2020).*
Yoshida et al. 2020 Nurse Education in Practice 44: article 1027 7 pages (Year: 2020).*
Lee 2017 IEEE Sensors Journal 17:6056-6068 (Year: 2017).*
International Search Report issued in PCT/JP2021/043235; mailed Feb. 15, 2022.
International Preliminary Report on Patentability (Chapter I) and Written Opinion of the International Searching Authority issued in PCT/JP2021/043235; issued May 30, 2023.

* cited by examiner

*Primary Examiner* — Keith M Raymond
*Assistant Examiner* — Patrick M Mehl
(74) *Attorney, Agent, or Firm* — Studebaker Brackett PLLC

(57) ABSTRACT

A swallowing evaluation system (1) includes an ultrasound probe (2), an image acquisition unit that acquires an ultrasound image in a pharynx of a subject by transmitting and receiving an ultrasound beam using the ultrasound probe (2), a sound acquisition unit that acquires a swallowing sound of the subject, and an evaluation unit (19) that evaluates swallowing of the subject using machine learning with a combination of the ultrasound image acquired by the image acquisition unit and the swallowing sound acquired by the sound acquisition unit.

16 Claims, 9 Drawing Sheets

SWALLOWING EVALUATION SYSTEM AND SWALLOWING EVALUATION METHOD

CROSS-REFERENCE TO RELATED APPLICATIONS

This application is a Continuation of PCT International Application No. PCT/JP2021/043235 filed on Nov. 25, 2021, which claims priority under 35 U.S.C. § 119(a) to Japanese Patent Application No. 2020-195807 filed on Nov. 26, 2020. The above applications are hereby expressly incorporated by reference, in their entirety, into the present application.

BACKGROUND OF THE INVENTION

1. Field of the Invention

The present invention relates to a swallowing evaluation system and a swallowing evaluation method for evaluating swallowing of a subject using an ultrasound image.

2. Description of the Related Art

In the related art, examination as to whether or not a subject can normally swallow has been performed using an ultrasound image obtained by imaging a pharynx part of the subject. Usually, in a case where swallowing is not normally performed, it is likely that food is remaining in an epiglottic vallecula or in a pyriform sinus of the subject. It is known that distinguishing the pyriform sinus and the residue of food from surrounding tissues in the ultrasound image is difficult. An examiner such as a doctor is required to have a certain degree of skill in order to check the pyriform sinus and the residue of food in the ultrasound image. In order to facilitate such examination, for example, a swallowing ability measurement system as disclosed in JP2020-089613A has been developed.

A swallowing ability measurement system in JP2020-089613A evaluates swallowing ability of a subject by acquiring an ultrasound image obtained by imaging an inside of a neck and a swallowing sound of the subject and by acquiring a movement speed of at least one of a tube wall of a tubular organ of a pharynx part of the subject or food passing through the tubular organ by temporally synchronizing an acquisition timing of the ultrasound image with a change in time of a frequency of the swallowing sound.

SUMMARY OF THE INVENTION

However, the timing at which the swallowing sound occurs varies depending on the subject. Thus, it may be difficult to accurately evaluate swallowing of the subject by simply temporally synchronizing the acquisition timing of the ultrasound image with the change in time of the frequency of the swallowing sound as in the technology disclosed in JP2020-089613A.

An object of the present invention is to provide a swallowing evaluation system and a swallowing evaluation method that can evaluate swallowing of a subject with high accuracy.

A swallowing evaluation system according to an aspect of the present invention comprises an ultrasound probe, an image acquisition unit that acquires an ultrasound image in a pharynx of a subject by transmitting and receiving an ultrasound beam using the ultrasound probe, a sound acquisition unit that acquires a swallowing sound of the subject, and an evaluation unit that evaluates swallowing of the subject using machine learning with a combination of the ultrasound image acquired by the image acquisition unit and the swallowing sound acquired by the sound acquisition unit.

It is preferable that the evaluation unit evaluates swallowing by inputting the ultrasound image and the swallowing sound into a neural network.

At this point, the evaluation unit may calculate an image feature amount by inputting the ultrasound image into a first neural network, calculate a sound feature amount by inputting the swallowing sound into a second neural network, and evaluate swallowing by inputting the image feature amount and the sound feature amount into a third neural network.

In addition, the evaluation unit may calculate a sound feature amount by inputting the swallowing sound into a second neural network and, in a case where the sound feature amount exceeds a determined sound feature amount threshold value, evaluate swallowing by inputting the ultrasound image and the sound feature amount into a fourth neural network.

In addition, the evaluation unit may calculate an image feature amount by inputting the ultrasound image into a first neural network and, in a case where the image feature amount exceeds a determined image feature amount threshold value, evaluate swallowing by inputting the swallowing sound and the image feature amount into a fifth neural network.

In addition, the evaluation unit may evaluate swallowing by inputting both of the ultrasound image and the swallowing sound into an identical neural network.

In addition, the evaluation unit may input time series data of the ultrasound image and of the swallowing sound into the neural network.

The sound acquisition unit may acquire a swallowing sound in swallowing, and the image acquisition unit may acquire an ultrasound image after swallowing.

Furthermore, the image acquisition unit may also acquire an ultrasound image in swallowing.

In addition, the sound acquisition unit may also acquire a breath sound of at least one of a breath sound before swallowing or a breath sound after swallowing.

The sound acquisition unit may include a microphone incorporated in the ultrasound probe.

In addition, the sound acquisition unit may include a microphone that is independent of the ultrasound probe and that is brought into contact with a pharynx part of the subject.

In addition, the evaluation unit may produce an output indicating whether or not a residue of swallowing is present in a pharynx part of the subject as an evaluation result.

In addition, the evaluation unit may produce an output indicating whether or not the subject has dysphagia as an evaluation result.

Furthermore, the evaluation unit may output hardness of food to be swallowed suitable for the subject as an evaluation result.

In addition, it is preferable that the swallowing evaluation system further comprises a monitor on which the ultrasound image acquired by the image acquisition unit and information representing the swallowing sound acquired by the sound acquisition unit are displayed.

A swallowing evaluation method according to another aspect of the present invention comprises acquiring an ultrasound image in a pharynx of a subject by transmitting and receiving an ultrasound beam using an ultrasound probe, acquiring a swallowing sound of the subject, and evaluating swallowing of the subject using machine learning with the acquired ultrasound image and the swallowing sound as an input.

According to the present invention, a swallowing evaluation system comprises an ultrasound probe, an image acquisition unit that acquires an ultrasound image in a pharynx of a subject by transmitting and receiving an ultrasound beam using the ultrasound probe, a sound acquisition unit that acquires a swallowing sound of the subject, and an evaluation unit that evaluates swallowing of the subject using machine learning with a combination of the ultrasound image acquired by the image acquisition unit and the swallowing sound acquired by the sound acquisition unit. Thus, swallowing of the subject can be evaluated with high accuracy.

DESCRIPTION OF THE PREFERRED EMBODIMENTS

Hereinafter, embodiments of the invention will be described with reference to the accompanying drawings.

The description of configuration requirements described below is provided based on the representative embodiment of the present invention, but the present invention is not limited to such an embodiment.

In the present specification, a numerical range represented using "to" means a range including the numerical values before and after "to" as a lower limit value and an upper limit value.

In the present specification, the terms "identical" and "same" include an error range generally allowed in the technical field.

Embodiment 1

Figure 1:
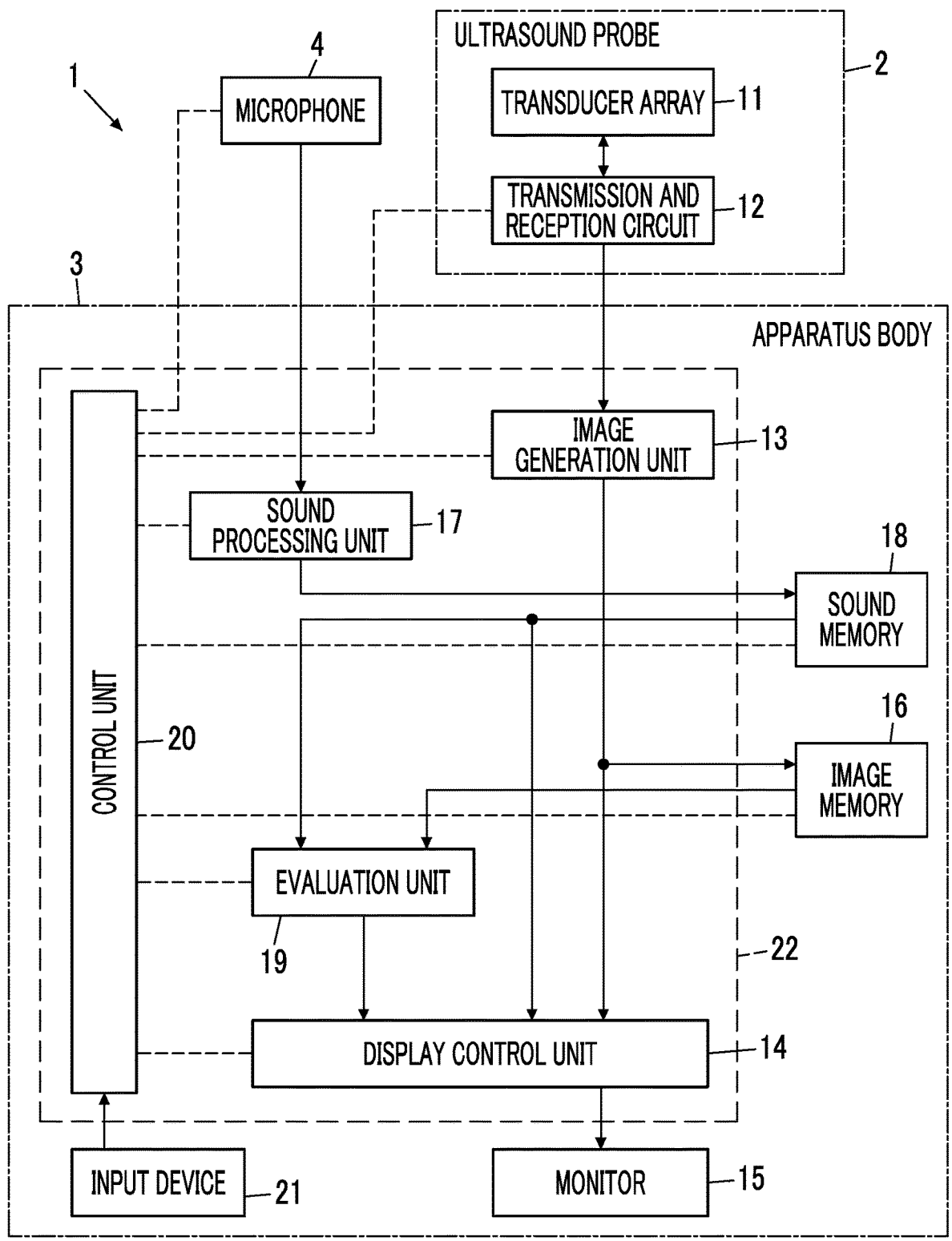
FIG. 1 is a block diagram illustrating a configuration of a swallowing evaluation system according to Embodiment 1 of the present invention.

FIG. 1 illustrates a configuration of a swallowing evaluation system 1 according to Embodiment 1 of the present invention. The swallowing evaluation system 1 comprises an ultrasound probe 2, an apparatus body 3, and a microphone 4. The ultrasound probe 2 and the apparatus body 3 are connected to each other, and the apparatus body 3 and the microphone 4 are connected to each other.

The ultrasound probe 2 includes a transducer array 11. A transmission and reception circuit 12 is connected to the transducer array 11.

The apparatus body 3 includes an image generation unit 13. The image generation unit 13 is connected to the transmission and reception circuit 12 of the ultrasound probe 2. The transmission and reception circuit 12 and the image generation unit 13 constitute an image acquisition unit. In addition, a display control unit 14 and a monitor 15 are sequentially connected to the image generation unit 13. In addition, an image memory 16 is connected to the image generation unit 13. In addition, the apparatus body 3 includes a sound processing unit 17, and the sound processing unit 17 is connected to the microphone 4. The microphone 4 and the sound processing unit 17 constitute a sound acquisition unit. In addition, a sound memory 18 is connected to the sound processing unit 17. The sound memory 18 is connected to the display control unit 14. In addition, an evaluation unit 19 is connected to the image memory 16 and to the sound memory 18, and the display control unit 14 is connected to the evaluation unit 19.

In addition, a control unit 20 is connected to the transmission and reception circuit 12, the image generation unit 13, the display control unit 14, the image memory 16, the sound processing unit 17, the sound memory 18, and the evaluation unit 19. In addition, an input device 21 is connected to the control unit 20.

In addition, the image generation unit 13, the display control unit 14, the sound processing unit 17, the evaluation unit 19, and the control unit 20 constitute a processor 22.

The transducer array 11 includes a plurality of oscillators that are one-dimensionally or two-dimensionally arranged. Each of these oscillators transmits an ultrasound wave in accordance with a drive signal supplied from the transmission and reception circuit 12, and receives an ultrasound echo from a subject and outputs a signal based on the ultrasound echo. Each oscillator is configured by forming an electrode at both ends of a piezoelectric body consisting of, for example, a piezoelectric ceramic represented by lead zirconate titanate (PZT), a polymer piezoelectric element represented by polyvinylidene difluoride (PVDF), and a piezoelectric single crystal represented by lead magnesium niobate-lead titanate (PMN-PT).

Figure 2:
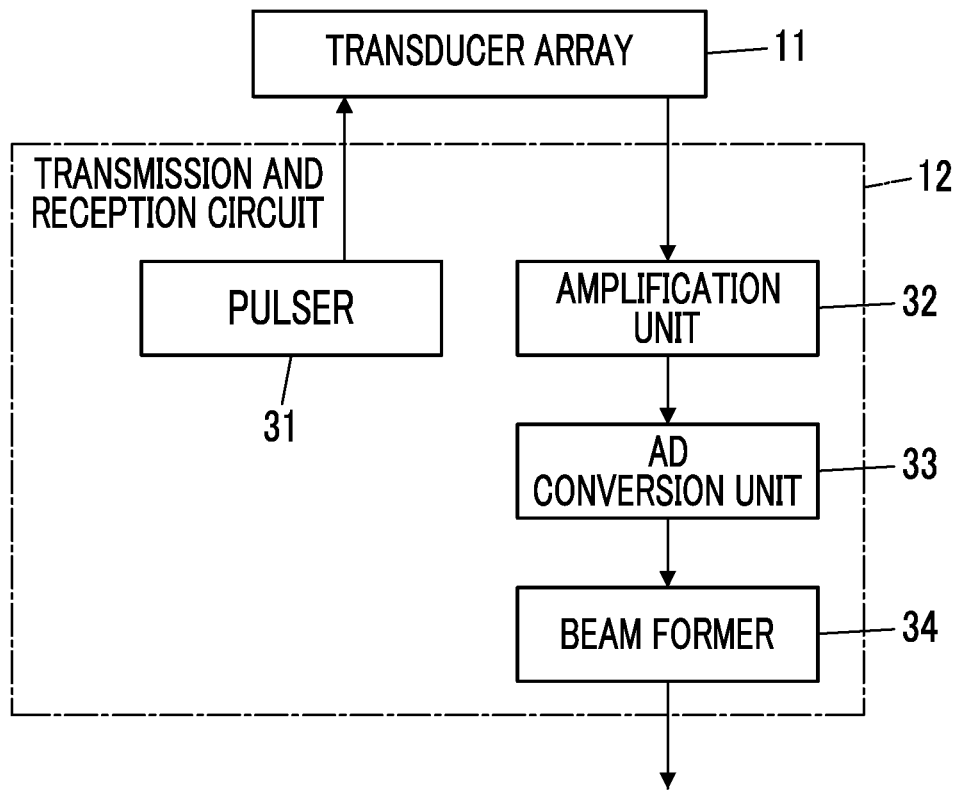
FIG. 2 is a block diagram illustrating a configuration of a transmission and reception circuit in Embodiment 1 of the present invention.

The transmission and reception circuit 12, under control of the control unit 20, transmits the ultrasound wave from the transducer array 11 and generates a sound ray signal based on a reception signal acquired by the transducer array 11. As illustrated in FIG. 2, the transmission and reception circuit 12 includes a pulser 31 connected to the transducer array 11, and an amplification unit 32, an analog digital (AD) conversion unit 33, and a beam former 34 that are sequentially connected in series from the transducer array 11.

The pulser 31 includes, for example, a plurality of pulse generators and supplies each drive signal to the plurality of oscillators by adjusting a delay amount of each drive signal based on a transmission delay pattern selected in accordance with a control signal from the control unit 20 so that the ultrasound waves transmitted from the plurality of oscillators of the transducer array 11 form an ultrasound beam. In a case where a voltage having a pulse shape or a continuous wave shape is applied to the electrodes of the oscillators of the transducer array 11, the piezoelectric body expands and contracts to generate an ultrasound wave having a pulse shape or a continuous wave shape from each oscillator, and an ultrasound beam is formed from a combined wave of the ultrasound waves.

The transmitted ultrasound beam is reflected by, for example, a target such as a part of the subject and propagates toward the transducer array 11 of the ultrasound probe 2. The ultrasound echo propagating toward the transducer array 11 is received by each oscillator constituting the transducer array 11. At this point, each oscillator constituting the transducer array 11, by receiving the propagating ultrasound echo, expands and contracts to generate the reception signal that is an electric signal and outputs the reception signal to the amplification unit 32.

The amplification unit 32 amplifies the signal input from each oscillator constituting the transducer array 11 and transmits the amplified signal to the AD conversion unit 33. The AD conversion unit 33 converts the signal transmitted from the amplification unit 32 into digital reception data and transmits the reception data to the beam former 34. The beam former 34 performs so-called reception focus processing by applying a delay to each reception data received from the AD conversion unit 33 and by adding each reception data in accordance with a sound speed or with a distribution of the sound speed set based on a reception delay pattern selected in accordance with the control signal from the control unit 20. Through the reception focus processing, the sound ray signal in which each reception data converted by the AD conversion unit 33 is phased and added, and in which a focus of the ultrasound echo is narrowed is acquired. The sound ray signal is transmitted to the image generation unit 13.

Figure 3:
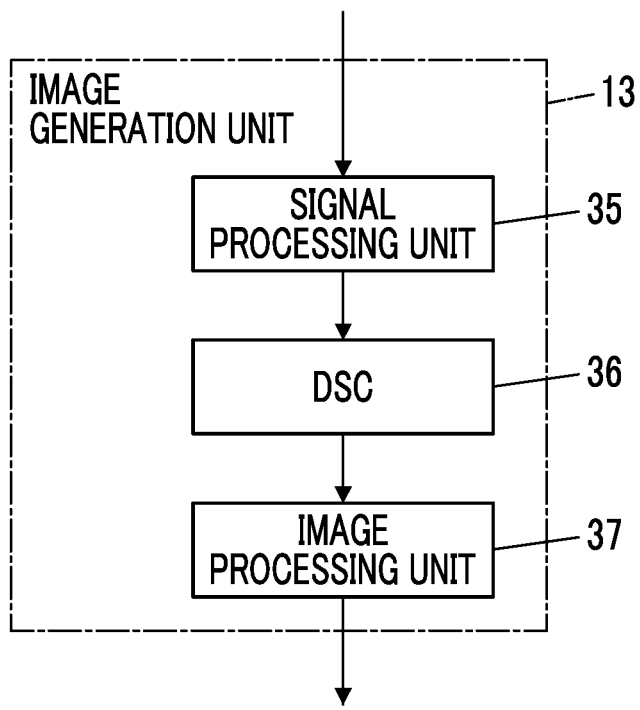
FIG. 3 is a block diagram illustrating a configuration of an image generation unit in Embodiment 1 of the present invention.

The image generation unit 13 has a configuration in which a signal processing unit 35, a digital scan converter (DSC) 36, and an image processing unit 37 are sequentially connected in series as illustrated in FIG. 3.

The signal processing unit 35 corrects attenuation by distance in accordance with depths of reflection positions of the ultrasound waves and then, performs envelope detection processing with respect to the sound ray signal transmitted from the transmission and reception circuit 12, thereby generating a B-mode image signal that is tomographic image information related to tissues inside the subject.

The DSC 36 converts the B-mode image signal generated by the signal processing unit 35 into an image signal complying with a scanning method of a typical television signal (raster conversion).

The image processing unit 37 performs various types of necessary image processing such as gradation processing on the B-mode image signal input from the DSC 36 and then, transmits the B-mode image signal to the display control unit 14 and to the image memory 16 in accordance with an instruction from the control unit 20. The B-mode image signal on which the image processing is performed by the image processing unit 37 will be simply referred to as an ultrasound image.

The image memory 16 is a memory for storing and reading out the ultrasound image generated by the image generation unit 13 under control of the control unit 20. The ultrasound image stored in the image memory 16 is read out under control of the control unit 20 and is transmitted to the evaluation unit 19.

For example, a recording medium such as a flash memory, a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory) can be used as the image memory 16.

The microphone 4 is disposed near a throat of the subject independently of the ultrasound probe 2 and acquires a swallowing sound of the subject as analog data. The swallowing sound of the subject acquired by the microphone 4 is transmitted to the sound processing unit 17.

For example, the microphone 4 can be manually brought into contact with a pharynx part of the subject by a user or can also be attached to the pharynx part of the subject. In addition, for example, the microphone 4 includes a mounting part, not illustrated, having a shape such as a frame shape to be mounted on a neck of the subject. The microphone 4 can be disposed near the pharynx part of the subject by mounting the mounting part on the neck of the subject.

The sound processing unit 17 converts the analog data of the swallowing sound acquired by the microphone 4 into digital data and transmits the obtained digital data to the sound memory 18. In addition, the sound processing unit 17 generates information representing the swallowing sound, such as a waveform graph representing a change in time of an amplitude of the swallowing sound, based on the digital data of the swallowing sound and transmits the information to the sound memory 18.

The sound memory 18 is a memory for storing and reading out the digital data of the swallowing sound transmitted from the sound processing unit 17 and the information such as the waveform graph representing the swallowing sound under control of the control unit 20. The data of the swallowing sound stored in the sound memory 18 is read out under control of the control unit 20 and is transmitted to the evaluation unit 19. In addition, the information representing the swallowing sound stored in the sound memory 18 is read out under control of the control unit 20 and is transmitted to the display control unit 14 to be displayed on the monitor 15.

The evaluation unit 19 evaluates swallowing of the subject using machine learning (multimodal learning) with a combination of the ultrasound image transmitted from the image memory 16 and the data of the swallowing sound of the subject transmitted from the sound memory 18.

Figure 4:
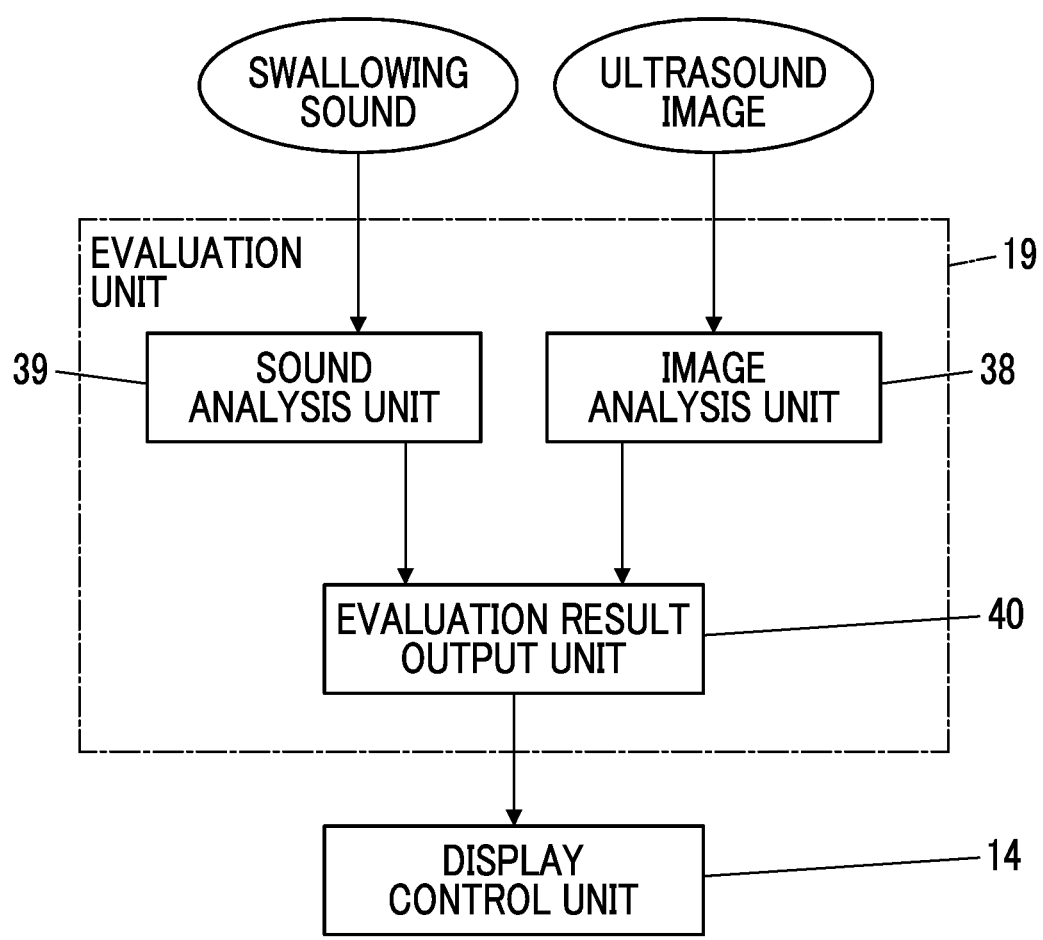
FIG. 4 is a block diagram illustrating a configuration of an evaluation unit in Embodiment 1 of the present invention.

As illustrated in FIG. 4, the evaluation unit 19 includes an image analysis unit 38, a sound analysis unit 39, and an evaluation result output unit 40. The evaluation result output unit 40 is connected to the image analysis unit 38 and to the sound analysis unit 39, and the display control unit 14 is connected to the evaluation result output unit 40.

The image analysis unit 38 receives the ultrasound image, which is obtained by imaging a pharynx of the subject, from the image memory 16 and calculates an image feature amount by inputting the ultrasound image into a trained first neural network. The image feature amount is an indicator that is calculated based on the ultrasound image and that represents a degree of abnormality occurring in swallowing of the subject, such as a probability of food remaining in the pharynx of the subject or a probability of the subject having dysphagia. As the image feature amount is increased, it can be determined that a probability of abnormality occurring in swallowing of the subject is increased. As the image feature amount is decreased, it can be determined that the probability of abnormality occurring in swallowing of the subject is decreased.

Here, usually, in a case where abnormality is occurring in swallowing of the subject, it is likely that food is remaining in an epiglottic vallecula or in a pyriform sinus in the pharynx of the subject. Thus, in a case where a food-like structure remaining in the epiglottic vallecula or in the pyriform sinus in the ultrasound image is recognized, it can be determined that a possibility of abnormality occurring in swallowing of the subject is high.

For example, based on ultrasound images obtained by imaging pharynges of a plurality of subjects including a case where food is remaining in the pyriform sinus and a case where food is not remaining in the pyriform sinus, the first neural network used by the image analysis unit 38 learns about a feature such as a structure depicted in the ultrasound images and outputs the image feature amount by comparing the learned feature with a feature in the input ultrasound image.

The sound analysis unit 39 receives the data of the swallowing sound of the subject from the sound memory 18 and calculates a sound feature amount by inputting the data of the swallowing sound into a trained second neural network. The sound feature amount is an indicator that is calculated based on the data of the swallowing sound of the subject and that represents a degree of abnormality occurring in swallowing of the subject, such as a probability of food remaining in the pharynx of the subject or a probability of the subject having dysphagia. As the sound feature amount is increased, it can be determined that a probability of abnormality occurring in swallowing of the subject is increased. As the sound feature amount is decreased, it can be determined that the probability of abnormality occurring in swallowing of the subject is decreased.

Here, in a case where abnormality is occurring in swallowing of the subject, it is likely that an abnormal noise sound is included, and that a sound having an abnormal frequency is included, compared to a case where the subject normally swallows. Thus, in a case where an abnormal noise sound is included in the swallowing sound, or in a case where a peak value of the amplitude is detected in an abnormal frequency band compared to that in a normal swallowing as a result of performing frequency analysis on the swallowing sound, it can be determined that a possibility of abnormality occurring in swallowing of the subject is high.

For example, the second neural network used by the sound analysis unit 39 outputs the sound feature amount by comparing a typical change in time of the amplitude and a typical frequency distribution of the normal swallowing sound learned based on data of swallowing sounds of a plurality of subjects with the change in time of the amplitude and a frequency distribution of the input swallowing sound, respectively.

The evaluation result output unit 40 outputs an evaluation result such as whether or not the subject has dysphagia by inputting the image feature amount calculated by the image analysis unit 38 and the sound feature amount calculated by the sound analysis unit 39 into a trained third neural network. The third neural network has learned about a relationship between a combination of a value of the image feature amount and a value of the sound feature amount, and the evaluation result related to swallowing of the subject based on evaluations of a plurality of subjects, and outputs the evaluation result of swallowing based on a learning result in a case where the image feature amount and the sound feature amount are input.

The control unit 20 controls each part of the swallowing evaluation system 1 in accordance with a program and the like recorded in advance.

The display control unit 14 displays the ultrasound image, the change in time of the amplitude of the swallowing sound of the subject, the evaluation result of swallowing, and the like on the monitor 15 by performing predetermined processing thereon under control of the control unit 20.

The monitor 15 performs various types of display under control of the display control unit 14. Examples of the monitor 15 include display devices such as a liquid crystal display (LCD) and an organic electroluminescence display (organic EL display).

The input device 21 is used for the user to perform an input operation. For example, the input device 21 is composed of a device such as a keyboard, a mouse, a trackball, a touchpad, and a touch panel for the user to perform the input operation.

The processor 22 including the image generation unit 13, the display control unit 14, the sound processing unit 17, the evaluation unit 19, and the control unit 20 is composed of a central processing unit (CPU) and a control program causing the CPU to perform various types of processing, but may also be configured using a field programmable gate array (FPGA), a digital signal processor (DSP), an application specific integrated circuit (ASIC), a graphics processing unit (GPU), or other integrated circuits (IC) or may also be composed of a combination thereof.

In addition, the image generation unit 13, the display control unit 14, the sound processing unit 17, the evaluation unit 19, and the control unit 20 of the processor 22 can also be configured to be integrated in one CPU or the like partially or as a whole.

Figure 5:
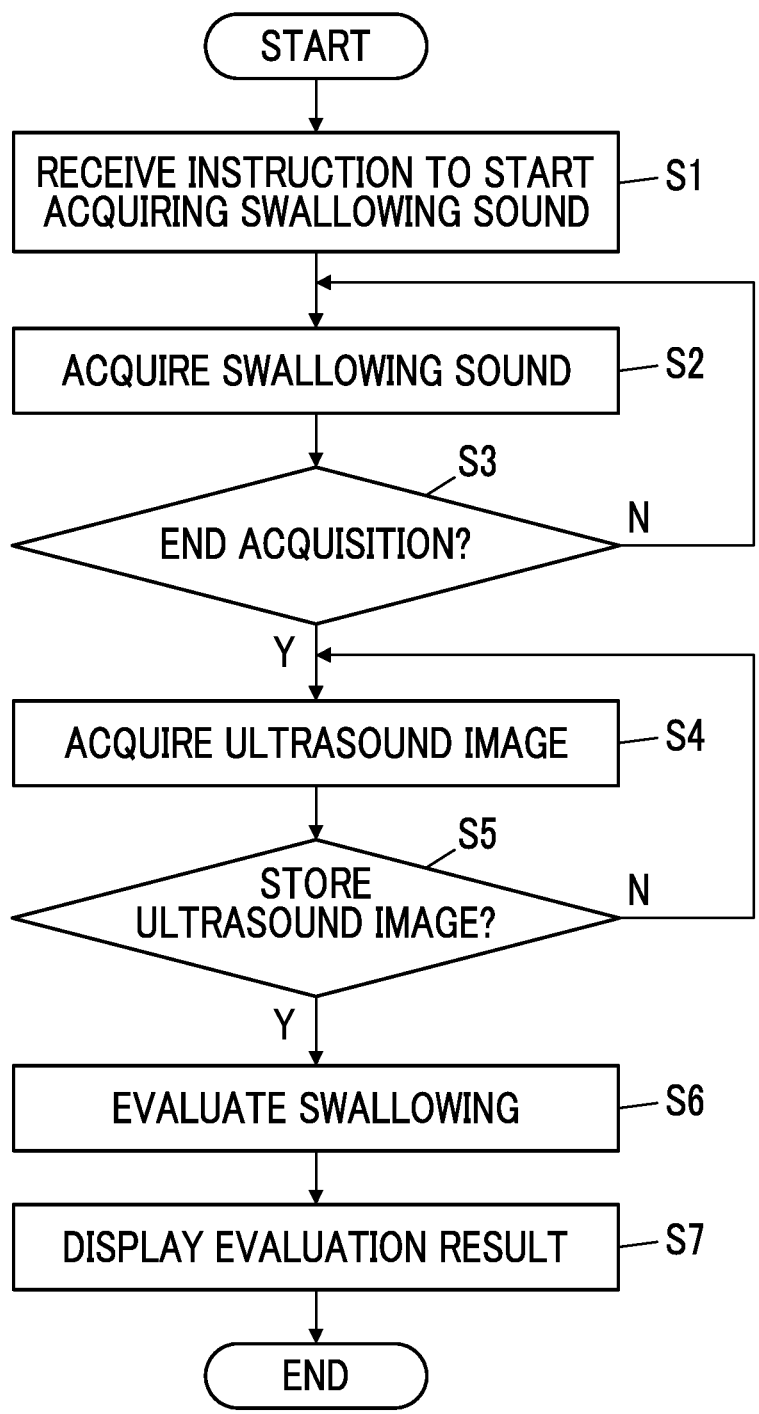
FIG. 5 is a flowchart illustrating operation of the swallowing evaluation system according to Embodiment 1 of the present invention.

Next, operation of the swallowing evaluation system 1 according to Embodiment 1 of the present invention will be described using the flowchart illustrated in FIG. 5.

First, the user brings the ultrasound probe 2 into contact with the throat of the subject and disposes the microphone 4 on the throat of the subject. In this state, in step S1, the control unit 20 receives an instruction to start acquiring the swallowing sound of the subject for evaluating the swallowing sound of the subject. For example, in a case where an instruction to start acquiring the swallowing sound is input by the user through the input device 21, the control unit 20 determines that the instruction is received.

In addition, at a timing at which step S1 is completed, for example, the user asks the subject to swallow food, and swallowing of the subject is started. Here, for example, jelly that is generally available for subjects having dysphagia is used as the food swallowed by the subject.

Figure 6:
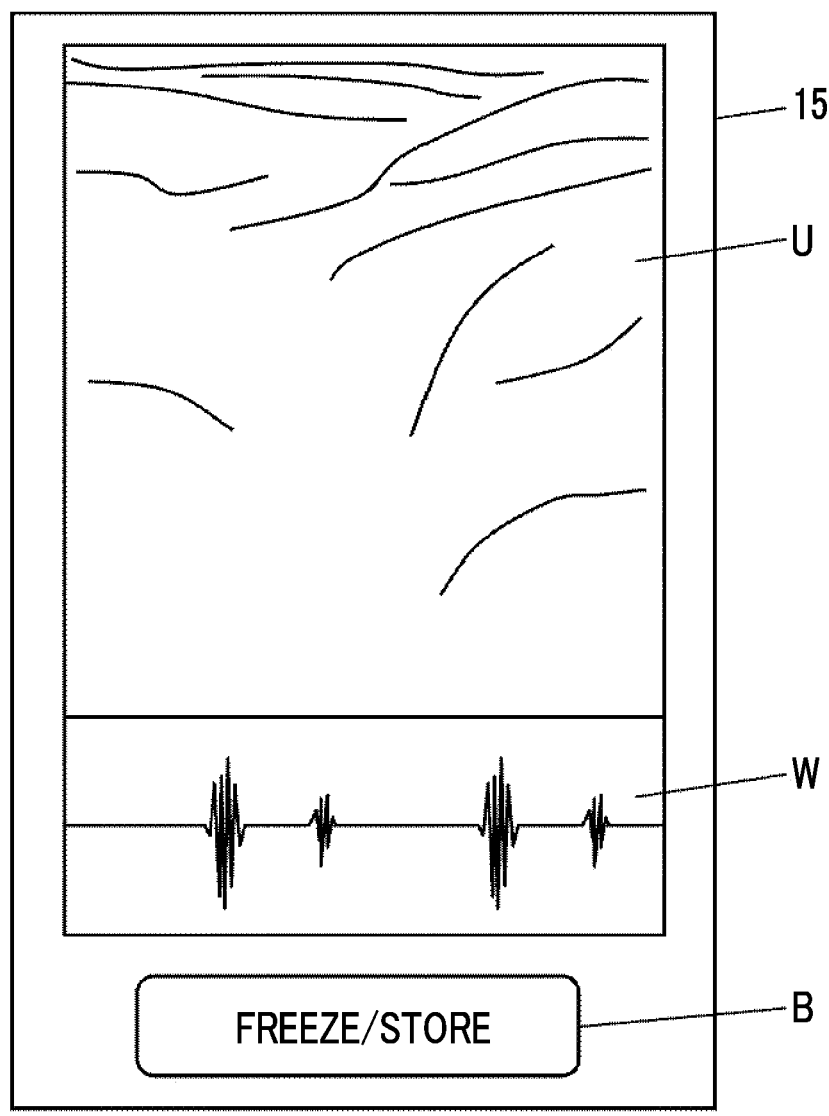
FIG. 6 is a diagram illustrating an example of displaying an ultrasound image and information representing a swallowing sound on a monitor.

Next, the swallowing sound in swallowing of the subject is acquired by the microphone 4. The analog data of the swallowing sound acquired by the microphone 4 is converted into digital data and is stored in the sound memory 18 by the sound processing unit 17. In addition, the information representing the swallowing sound, such as the waveform graph representing the change in time of the amplitude of the swallowing sound, is generated by the sound processing unit 17. For example, the information is displayed on the monitor 15 as illustrated in FIG. 6. In the example in FIG. 6, a waveform graph W representing the change in time of the amplitude of the swallowing sound is displayed as the information representing the swallowing sound.

In step S3, the control unit 20 determines whether or not to end the acquisition of the swallowing sound. For example, in a case where an instruction to end the acquisition of the swallowing sound is input by the user through the input device 21, the control unit 20 determines to end the acquisition of the swallowing sound. In a case where the instruction to end the acquisition of the swallowing sound is not input by the user through the input device 21, the control unit 20 determines to continue acquiring the swallowing sound.

In a case where it is determined to continue acquiring the swallowing sound in step S3, a return is made to step S2, and the swallowing sound is newly acquired. Processing of step S2 and step S3 is repeated until it is determined to end the acquisition of the swallowing sound in step S3. Accordingly, the swallowing sound in swallowing of the subject acquired by repeating step S2 and step S3 is stored in the sound memory 18.

In step S3, for example, in a case where it is determined to end the acquisition of the swallowing sound because the user determines that swallowing of the subject ends, and inputs the instruction to end the acquisition of the swallowing sound through the input device 21, a transition is made to step S4.

In step S4, an ultrasound image U obtained by imaging the pharynx of the subject after swallowing is acquired. By acquiring the ultrasound image U after swallowing of the subject, it is likely that the ultrasound image U in which food remaining in the pyriform sinus is depicted is obtained in a case where any kind of abnormality is occurring in swallowing of the subject.

In capturing the ultrasound image U, the transmission and reception circuit 12 generates the sound ray signal by performing the reception focus processing using a sound speed value, set in advance, under control of the control unit 20. The sound ray signal generated by the transmission and reception circuit 12 in such a manner is transmitted to the image generation unit 13. The image generation unit 13 generates the ultrasound image using the sound ray signal transmitted from the transmission and reception circuit 12. For example, as illustrated in FIG. 6, the ultrasound image U generated in such a manner is transmitted to the display control unit 14 to be displayed on the monitor 15.

In step S5, the control unit 20 determines whether or not to store the ultrasound image U acquired in step S4 in the image memory 16. For example, in a case where the user inputs an instruction to store the ultrasound image U through the input device 21, the control unit 20 determines to store the ultrasound image U acquired in step S4 and stores the ultrasound image U in the image memory 16. In a case where the user does not input the instruction to store the ultrasound image U through the input device 21, the control unit 20 determines not to store the ultrasound image U acquired in step S4.

For example, as illustrated in FIG. 6, the control unit 20 can display a freeze and store button B on the monitor 15. In a case where the freeze and store button B is selected by the user through the input device 21, the control unit 20 can freeze and display the ultrasound image U displayed on the monitor 15 and store the ultrasound image U in the image memory 16. In a case where the freeze and store button B is not selected, the control unit 20 can determine not to store the ultrasound image U.

In a case where it is determined not to store the ultrasound image U in step S5, a return is made to step S4, and the ultrasound image U is newly acquired. Thus, processing of step S4 and step S5 is repeated until it is determined to store the ultrasound image U in step S5.

In a case where it is determined to store the ultrasound image U in step S5, and the ultrasound image U is stored in the image memory 16, a transition is made to step S6.

In step S6, the evaluation unit 19 evaluates swallowing of the subject using machine learning with a combination of the data of the swallowing sound in swallowing of the subject, which is stored in the sound memory 18 by repeating step S2 and step S3, and the ultrasound image U stored in the image memory 16 in step S5.

Processing of step S6 will be described in detail using the flowchart illustrated in FIG. 7.

In a case where processing of step S6 is started, processing of step S8 is performed first.

In step S8, the image analysis unit 38 of the evaluation unit 19 calculates the image feature amount representing the degree of abnormality occurring in swallowing of the subject by inputting the ultrasound image U stored in the image memory 16 in step S5 into the first neural network.

At this point, for example, the first neural network outputs a probability that remaining food is depicted in the ultrasound image U, as the image feature amount by comparing the feature in the ultrasound images, which is learned based on the ultrasound images obtained by imaging the pharynges of the plurality of subjects including a case where food is remaining in the pyriform sinus and a case where food is not remaining in the pyriform sinus, with the feature in the input ultrasound image U. For example, as the remaining food-like structure is more clearly depicted in the ultrasound image U, a higher value of the image feature amount is obtained.

Next, in step S9, the sound analysis unit 39 of the evaluation unit 19 calculates the sound feature amount representing the degree of abnormality occurring in swallowing of the subject by inputting the data of the swallowing sound in swallowing of the subject acquired by repeating step S2 and step S3 into the second neural network.

At this point, for example, the second neural network outputs the sound feature amount by comparing the typical change in time of the amplitude and the typical frequency distribution of the normal swallowing sound learned based on the data of the swallowing sounds of the plurality of subjects with the change in time of the amplitude and the frequency distribution of the input swallowing sound, respectively. For example, as an amplitude of the noise sound is detected at a more abnormal timing compared to the typical change in time of the amplitude of the normal swallowing sound, or as the peak value of the amplitude is detected in a more abnormal frequency band compared to the typical frequency distribution of the normal swallowing sound, a higher value of the sound feature amount is obtained.

Next, in step S10, the evaluation result output unit 40 of the evaluation unit 19 outputs the evaluation result of swallowing of the subject by inputting the image feature amount calculated in step S8 and the sound feature amount calculated in step S9 into the third neural network. For example, an output indicating whether or not there is remaining food in the pyriform sinus or whether or not dysphagia is suspected in the subject is produced as the evaluation result of swallowing. In addition, for example, the evaluation result output unit 40 can also output, as the evaluation result of swallowing, an amount of food remaining in the pyriform sinus in a plurality of levels such as "no remaining", "small amount remaining", "large amount remaining", and "very large amount remaining". In addition, for example, the evaluation result output unit 40 can also output hardness of food to be swallowed suitable for the evaluated subject as the evaluation result of swallowing. For example, hardness of food to be swallowed disclosed in "Japanese Dysphagia Diet 2013 by the JSDR dysphagia diet committee, The Japanese Journal of Dysphagia Rehabilitation 17(3): 255-267, 2013" can be used as the hardness of food to be swallowed.

In such a manner, in step S10, the final evaluation result of swallowing of the subject is output based on both of the image feature amount which represents the degree of abnormality occurring in swallowing of the subject and which is calculated based on the analysis of the ultrasound image U, and the sound feature amount which represents the degree of abnormality occurring in swallowing of the subject and which is calculated based on the analysis of the swallowing sound of the subject. Thus, for example, it is possible to obtain the evaluation result with higher accuracy than in the evaluation of swallowing of the subject using only one of the image feature amount calculated based on the analysis of the ultrasound image U and the sound feature amount calculated based on the analysis of the swallowing sound of the subject.

By performing processing of step S8 to step S10 in such a manner, processing of step S6 is performed. In a case where processing of step S6 is completed, a transition is made to step S7.

In step S7, information representing the evaluation result of swallowing of the subject output in step S6 is displayed on the monitor 15.

Accordingly, the operation of the swallowing evaluation system 1 according to Embodiment 1 is completed.

From the above, according to the swallowing evaluation system 1 according to Embodiment 1 of the present invention, since swallowing of the subject is evaluated by machine learning with a combination of both of the ultrasound image U obtained by imaging the pharynx of the subject and the swallowing sound of the subject, swallowing of the subject can be evaluated with high accuracy.

The transmission and reception circuit 12 is comprised in the ultrasound probe 2 as illustrated in FIG. 1 but may be comprised in the apparatus body 3 instead of being comprised in the ultrasound probe 2.

In addition, the image generation unit 13 is comprised in the apparatus body 3 but may be comprised in the ultrasound probe 2 instead of being comprised in the apparatus body 3.

In addition, as illustrated in FIG. 3, while the image generation unit 13 comprises the signal processing unit 35, the DSC 36, and the image processing unit 37, the signal processing unit 35 can be included in the ultrasound probe 2.

In addition, a connection method between the ultrasound probe 2 and the apparatus body 3 is not particularly limited and may be wired connection or wireless connection. In addition, a connection method between the apparatus body 3 and the microphone 4 is not particularly limited and may be wired connection or wireless connection.

In addition, the apparatus body 3 may be of a so-called handheld type that can be easily carried by the user, or may be of a so-called stationary type.

In addition, the microphone 4 is described as being independent of the ultrasound probe 2 but may be attached to the ultrasound probe 2 by, for example, incorporating the microphone 4 in the ultrasound probe 2. In this case, the microphone 4 does not need to be independently disposed near the pharynx part of the subject, and the swallowing sound of the subject can be acquired by bringing the ultrasound probe 2 into contact with the pharynx part of the subject for capturing the ultrasound image U.

In addition, while the sound acquisition unit for acquiring the swallowing sound of the subject is described as being composed of the sound processing unit 17 of the apparatus body 3 and of the microphone 4, the swallowing evaluation system 1 can comprise the sound acquisition unit that includes the microphone 4 and the sound processing unit 17 and that is independent of the apparatus body 3. In this case, the data of the swallowing sound of the subject acquired by the sound acquisition unit is input into the apparatus body 3.

In addition, while the ultrasound image U after swallowing of the subject is acquired and stored after the swallowing sound in swallowing of the subject is acquired and stored in step S2 to step S5, the ultrasound image U in swallowing of the subject may also be acquired and stored. In this case, in calculating the image feature amount in step S8, the ultrasound image U in swallowing can also be analyzed in addition to the ultrasound image U after swallowing. Thus, accuracy of the image feature amount can be improved.

In addition, the ultrasound images U of a plurality of continuous frames in a certain time from the start of swallowing to the end of swallowing of the subject can be acquired, and the ultrasound images U can be stored in the image memory 16. In this case, the image feature amount can be calculated by analyzing time series data of the ultrasound images U acquired within the certain time in step S8. Accordingly, for example, a motion of the structure in the pharynx can be analyzed based on the ultrasound images of the plurality of frames. Thus, for example, the image feature amount can be calculated with higher accuracy than in the calculation of the image feature amount based on the ultrasound image U of one frame.

In addition, in a case where any kind of abnormality is occurring in swallowing of the subject, it is considered that an abnormal noise sound is included in a breath sound, and that an abnormal breath sound is acquired, compared to a case where swallowing is normally performed. Thus, for example, in addition to the acquisition of the data of the swallowing sound in swallowing by the sound acquisition unit including the microphone 4 and the sound processing unit 17, data of a breath sound before swallowing and data of a breath sound after swallowing can be acquired, and the data of the breath sounds can be stored in the sound memory 18. In this case, the sound feature amount is calculated by analyzing the data of the swallowing sound and the data of the breath sounds of the subject in step S9. Accordingly, for example, the sound feature amount can be calculated with higher accuracy than in the calculation of the sound feature amount based on the swallowing sound of the subject.

Figure 7:
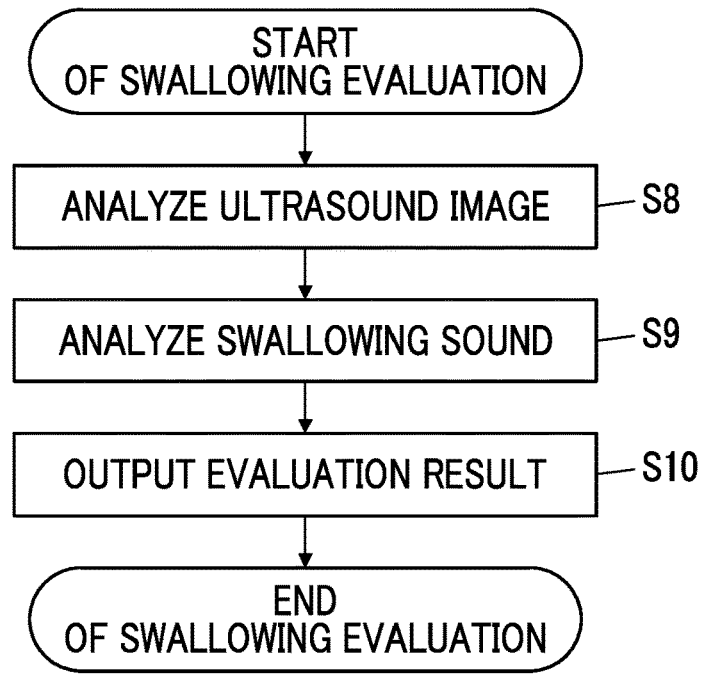
FIG. 7 is a flowchart illustrating detailed operation of swallowing evaluation in Embodiment 1 of the present invention.

In addition, while step S9 is performed after step S8 in the flowchart illustrated in FIG. 7, step S8 may be performed after step S9, or step S8 and step S9 may be performed at the same time.

In addition, a method of notifying the user of an output result of the evaluation result is not limited to the method of displaying the evaluation result on the monitor 15. For example, a lamp, not illustrated, can be provided in the swallowing evaluation system 1, and the user can be notified of, for example, whether or not the subject has dysphagia by a light emission color, a turn-on and turn-off pattern, or the like of the lamp. At this point, for example, the lamp may be disposed in the ultrasound probe 2, may be disposed in the apparatus body 3, or may be disposed independently of the ultrasound probe 2 and of the apparatus body 3.

Embodiment 2

In Embodiment 1, the evaluation unit 19 includes the image analysis unit 38, the sound analysis unit 39, and the evaluation result output unit 40 and evaluates swallowing of the subject using three neural networks of the first neural network, the second neural network, and the third neural network. However, a method of evaluating swallowing of the subject is not limited thereto.

For example, the evaluation unit 19 can evaluate swallowing of the subject using only an identical neural network that has learned about the ultrasound image U of the subject, the swallowing sound of the subject, and a relationship between a combination thereof and the evaluation result.

In the swallowing evaluation system 1, even in a case where the evaluation result of swallowing is output using only one neural network, swallowing of the subject is evaluated by machine learning with a combination of both of the ultrasound image U obtained by imaging the pharynx of the subject and the swallowing sound of the subject as in the case of using three neural networks as in Embodiment 1. Thus, swallowing of the subject can be evaluated with high accuracy.

Embodiment 3

For example, an evaluation of swallowing of the subject can be output using two neural networks.

Figure 8:
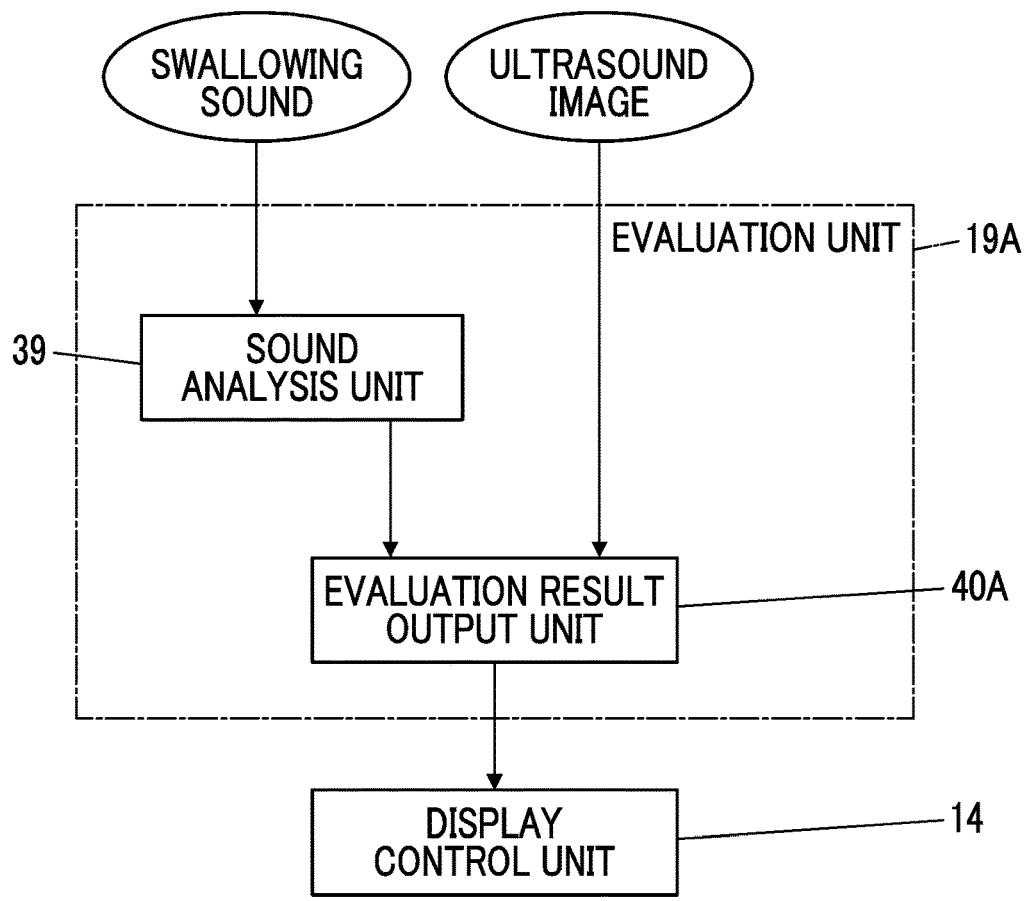
FIG. 8 is a block diagram illustrating a configuration of an evaluation unit in Embodiment 3 of the present invention.

FIG. 8 illustrates a configuration of an evaluation unit 19A in Embodiment 3. The evaluation unit 19A includes the sound analysis unit 39 and an evaluation result output unit 40A, and the evaluation result output unit 40A is connected to the sound analysis unit 39. In addition, the display control unit 14 is connected to the evaluation result output unit 40A.

In the same manner as the sound analysis unit 39 in Embodiment 1, the sound analysis unit 39 receives the data of the swallowing sound of the subject and calculates the sound feature amount by inputting the data of the swallowing sound into the second neural network. The calculated sound feature amount is output to the evaluation result output unit 40A.

The evaluation result output unit 40A has a sound feature amount threshold value that is determined with respect to the sound feature amount, and determines whether or not the sound feature amount calculated by the sound analysis unit 39 exceeds the sound feature amount threshold value. In addition, in a case where the sound feature amount calculated by the sound analysis unit 39 exceeds the sound feature amount threshold value, the evaluation result output unit 40A outputs the evaluation result of swallowing of the subject by inputting the sound feature amount and the ultrasound image U generated by the image generation unit 13 into a fourth neural network.

The fourth neural network used by the evaluation result output unit 40A calculates the image feature amount by analyzing the input ultrasound image U in the same manner as the first neural network used by the image analysis unit 38 in Embodiment 1, and outputs the evaluation result of swallowing of the subject based on the calculated image feature amount and the sound feature amount transmitted from the sound analysis unit 39 in the same manner as the third neural network used by the evaluation result output unit 40 in Embodiment 1.

Figure 9:
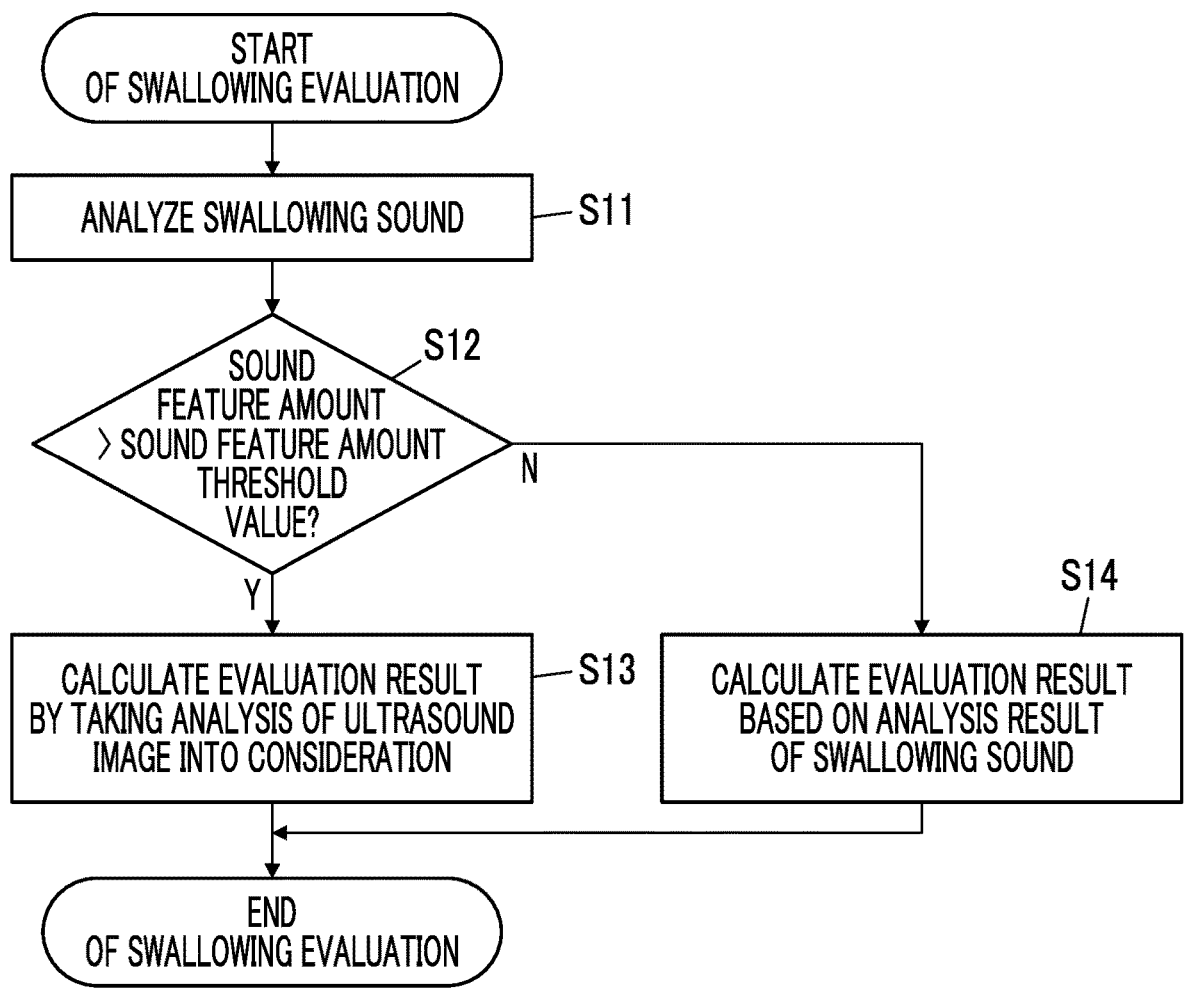
FIG. 9 is a flowchart illustrating detailed operation of swallowing evaluation in Embodiment 3 of the present invention.

Next, operation of swallowing evaluation in Embodiment 3 will be described using the flowchart illustrated in FIG. 9.

First, in step S11, the sound analysis unit 39 calculates the sound feature amount by inputting the data of the swallowing sound of the subject into the second neural network.

In step S12, the evaluation result output unit 40A determines whether or not the sound feature amount calculated in step S11 exceeds the sound feature amount threshold value. In a case where it is determined that the sound feature amount calculated in step S11 exceeds the sound feature amount threshold value, the evaluation result output unit 40A determines that a possibility of any kind of abnormality occurring in swallowing of the subject is high, and performs processing of step S13.

In step S13, the evaluation result output unit 40A outputs the evaluation result of swallowing into which an analysis result of the ultrasound image U is taken into consideration, by inputting the sound feature amount calculated in step S11 and the ultrasound image U obtained by imaging the pharynx of the subject into the fourth neural network.

In addition, in step S12, in a case where it is determined that the sound feature amount is less than or equal to the sound feature amount threshold value, the evaluation result output unit 40A determines that a possibility of abnormality occurring in swallowing of the subject is low, and performs processing of step S14.

In step S14, the evaluation result output unit 40A calculates the evaluation result of swallowing based on an analysis result of the swallowing sound in step S11. For example, the evaluation result output unit 40A, without using the fourth neural network, determines that a possibility of abnormality occurring in swallowing of the subject is low based on a result indicating that the sound feature amount is less than or equal to the sound feature amount threshold value in step S12, and outputs the evaluation result indicating that abnormality is not occurring in swallowing of the subject.

In this case, the evaluation result output unit 40A can output the evaluation result of swallowing of the subject using only the second neural network.

In such a manner, the operation of the swallowing evaluation in Embodiment 3 is ended.

In Embodiment 3, two neural networks of the second neural network and the fourth neural network are used only in a case where the sound feature amount exceeds the sound feature amount threshold value. In a case where the sound feature amount is less than or equal to the sound feature amount threshold value, only the second neural network is used. Thus, a calculation load of the processor 22 in using neural networks can be reduced, compared to that in Embodiment 1. Thus, in Embodiment 3, a processing time and power that are necessary for evaluating swallowing of the subject and that are caused by the calculation load of the processor 22 can be reduced.

Here, in a case where the apparatus body 3 is of a so-called handheld type or of a portable type, it is preferable that power is supplied to each part of the apparatus body 3 by a battery, not illustrated, that is easily carried. In addition, in a case where the apparatus body 3 is of a handheld type or of a portable type, a size of the apparatus body 3 is small compared to a case where the apparatus body 3 is of a so-called stationary type. Thus, it is easy to mount the processor 22 that has a large size and high operation performance. Thus, the aspect of Embodiment 3 is particularly useful in a case where the apparatus body 3 is of a handheld type or of a portable type.

In addition, usually, it is known that food that remains in the pyriform sinus and in the pharynx is not easily differentiated from surrounding tissues in the ultrasound image U obtained by imaging the pharynx of the subject. On the other hand, the swallowing sound can be acquired with relatively higher sensitivity. Thus, a more accurate determination can be made by determining whether or not abnormality is occurring in swallowing of the subject based on the swallowing sound than based on the ultrasound image U. In Embodiment 3, first, the sound feature amount is calculated, and the swallowing sound is evaluated by taking the analysis result of the ultrasound image U into consideration in a case where the calculated sound feature amount exceeds the sound feature amount threshold value. Thus, swallowing of the subject can be evaluated with high accuracy.

Embodiment 4

Figure 10:
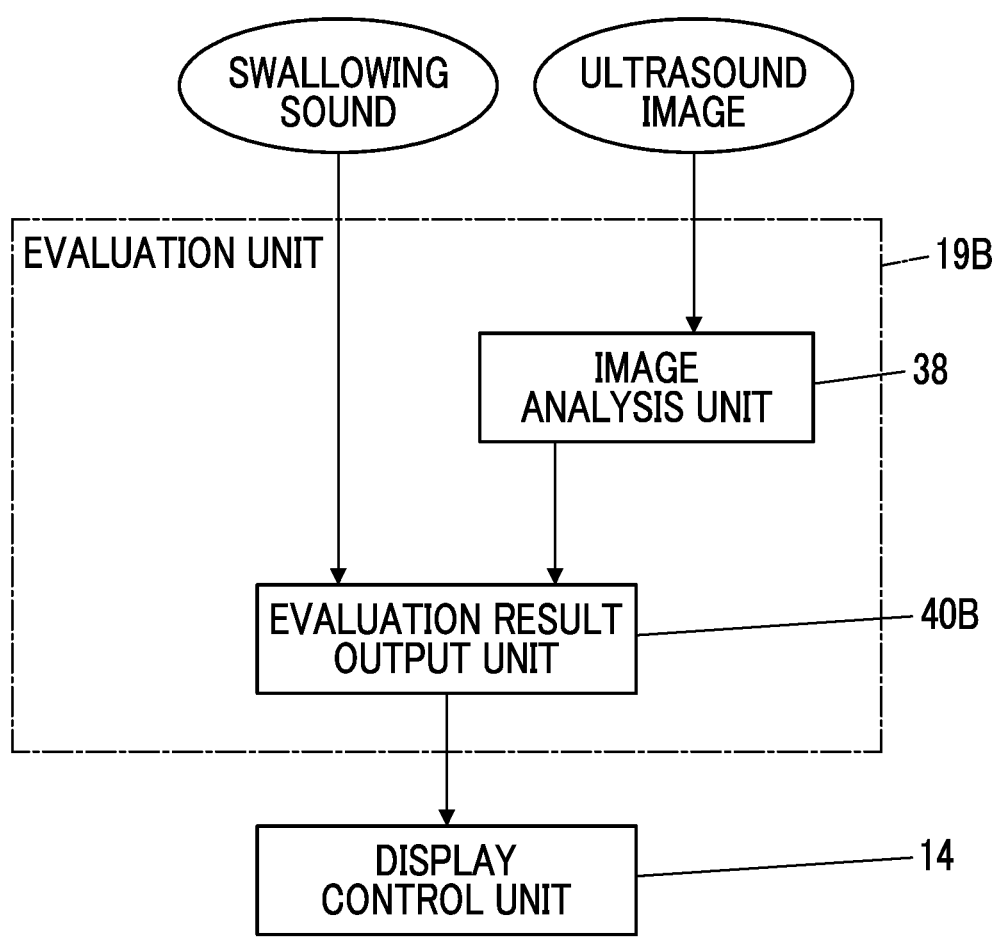
FIG. 10 is a block diagram illustrating a configuration of an evaluation unit in Embodiment 4 of the present invention.

FIG. 10 illustrates a configuration of an evaluation unit 19B in Embodiment 4. The evaluation unit 19B includes the image analysis unit 38 and an evaluation result output unit 40B, and the evaluation result output unit 40B is connected to the image analysis unit 38. In addition, the display control unit 14 is connected to the evaluation result output unit 40B.

In the same manner as the image analysis unit 38 in Embodiment 1, the image analysis unit 38 receives the ultrasound image U obtained by imaging the pharynx of the subject and calculates the image feature amount by inputting the ultrasound image U into the first neural network. The calculated image feature amount is output to the evaluation result output unit 40B.

The evaluation result output unit 40B has an image feature amount threshold value that is determined with respect to the image feature amount, and determines whether or not the image feature amount calculated by the image analysis unit 38 exceeds the image feature amount threshold value. In addition, in a case where the image feature amount calculated by the image analysis unit 38 exceeds the image feature amount threshold value, the evaluation result output unit 40B outputs the evaluation result of swallowing of the subject by inputting the image feature amount and the data of the swallowing sound of the subject acquired by the sound acquisition unit including the microphone 4 and the sound processing unit 17 into a fifth neural network.

The fifth neural network used by the evaluation result output unit 40B calculates the sound feature amount by analyzing the input data of the swallowing sound in the same manner as the second neural network used by the sound analysis unit 39 in Embodiment 1, and outputs the evaluation result of swallowing of the subject based on the calculated sound feature amount and the image feature amount transmitted from the image analysis unit 38 in the same manner as the third neural network used by the evaluation result output unit 40 in Embodiment 1.

Figure 11:
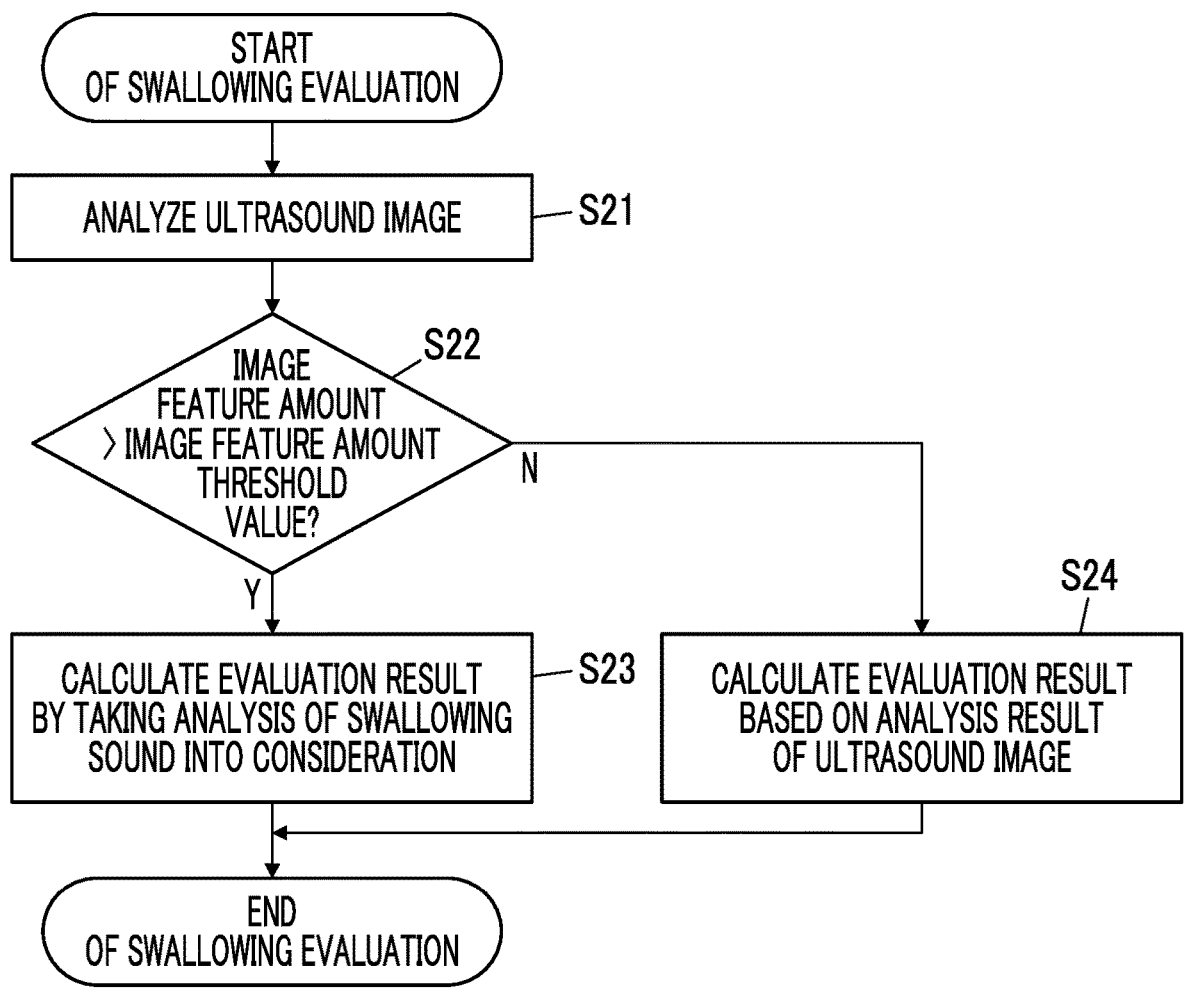
FIG. 11 is a flowchart illustrating detailed operation of swallowing evaluation in Embodiment 4 of the present invention.

Next, operation of swallowing evaluation in Embodiment 4 will be described using the flowchart illustrated in FIG. 11.

First, in step S21, the image analysis unit 38 calculates the image feature amount by inputting the ultrasound image U obtained by imaging the pharynx of the subject into the first neural network.

In step S22, the evaluation result output unit 40B determines whether or not the image feature amount calculated in step S21 exceeds the image feature amount threshold value. In step S22, in a case where it is determined that the image feature amount calculated in step S21 exceeds the image feature amount threshold value, the evaluation result output unit 40B determines that a possibility of any kind of abnormality occurring in swallowing of the subject is high, and performs processing of step S23.

In step S23, the evaluation result output unit 40B outputs the evaluation result of swallowing into which the analysis result of the swallowing sound is taken into consideration, by inputting the image feature amount calculated in step S21 and the data of the swallowing sound of the subject into the fifth neural network.

In addition, in step S22, in a case where it is determined that the image feature amount is less than or equal to the image feature amount threshold value, the evaluation result output unit 40B determines that a possibility of abnormality occurring in swallowing of the subject is low, and performs processing of step S24.

In step S24, the evaluation result output unit 40B calculates the evaluation result of swallowing based on the analysis result of the swallowing sound in step S21. For example, the evaluation result output unit 40B, without using the fifth neural network, determines that a possibility of abnormality occurring in swallowing of the subject is low based on a result indicating that the image feature amount is less than or equal to the image feature amount threshold value in step S22, and outputs the evaluation result indicating that abnormality is not occurring in swallowing of the subject.

In this case, the evaluation result output unit 40B can output the evaluation result of swallowing of the subject using only the first neural network.

In such a manner, the operation of the swallowing evaluation in Embodiment 4 is ended.

In Embodiment 4, two neural networks of the first neural network and the fifth neural network are used only in a case where the image feature amount exceeds the image feature amount threshold value. In a case where the image feature amount is less than or equal to the image feature amount threshold value, only the first neural network is used. Thus, the calculation load of the processor 22 in using neural networks can be reduced, compared to that in Embodiment 1. Thus, in Embodiment 4, the processing time and the power that are necessary for evaluating swallowing of the subject and that are caused by the calculation load of the processor 22 can be reduced as in Embodiment 3.

In addition, from the above, the aspect of Embodiment 4 is particularly useful in a case where the apparatus body 3 is of a handheld type or of a portable type as in the aspect of Embodiment 3.

EXPLANATION OF REFERENCES

1: swallowing evaluation system
2: ultrasound probe
3: apparatus body
4: microphone
11: transducer array
12: transmission and reception circuit
13: image generation unit
14: display control unit
15: monitor
16: image memory
17: sound processing unit
18: sound memory
19, 19A, 19B: evaluation unit
20: control unit
21: input device
22: processor
31: pulser
32: amplification unit
33: AD conversion unit
34: beam former
35: signal processing unit
36: DSC
37: image processing unit
38: image analysis unit
39: sound analysis unit
40, 40A, 40B: evaluation result output unit
B: freeze and store button
U: ultrasound image
W: waveform graph

What is claimed is:

1. A swallowing evaluation system comprising:
a memory configured to store computer-readable instructions, which when executed cause the swallowing evaluation system to evaluate swallowing of a subject; and
a processor configured to, when executing the computer-readable instructions, control the swallowing evaluation system to acquire an ultrasound image in a pharynx of the subject,
acquire a swallowing sound of the subject,
determine by inputting the ultrasound image into a neural network an image feature amount that represents a first degree of abnormality occurring in the swallowing of the subject, determine by inputting the swallowing sound into the neural network a sound feature amount that represents a second degree of abnormality occurring in the swallowing of the subject,
determine based on the first degree of abnormality and the second degree of abnormality at least one of a first evaluation whether a food-like structure remains in an epiglottic vallecula or a pyriform sinus of the subject and a second evaluation whether dysphagia is suspected in the subject, and
output a swallowing evaluation of the subject indicating at least one of the first evaluation and the second evaluation, and
the neural network being a trained neural network trained to determine the first degree of abnormality using images of pharynges of other subjects and trained to determine the second degree of abnormality using swallowing sounds of the other subjects.

2. The swallowing evaluation system according to claim 1,
wherein the neural network comprises:
a first neural network configured to calculate the image feature amount;
a second neural network configured to calculate the sound feature amount; and
a third neural network configured to determine the at least one of the first evaluation and the second evaluation based on the image feature amount and the sound feature amount.

3. The swallowing evaluation system according to claim 1,
wherein the neural network is a single neural network.

4. The swallowing evaluation system according to claim 1,
wherein the ultrasound image comprises a time series of ultrasound images of the subject and the swallowing sound comprises a time series of swallowing sounds of the subject.

5. The swallowing evaluation system according to claim 1,
wherein the swallowing sound comprises a swallowing sound during swallowing of the subject, and
the ultrasound image comprises an ultrasound image after the swallowing of the subject.

6. The swallowing evaluation system according to claim 5,
wherein the ultrasound image comprises a first ultrasound image during swallowing of the subject and a second ultrasound image after the swallowing of the subject.

7. The swallowing evaluation system according to claim 1,
wherein the processor when executing the computer-readable instructions is further configured to control the swallowing evaluation system to acquire a breath sound of at least one of a first breath sound before swallowing of the subject and a second breath sound after the swallowing of the subject, and determine based on the breath sound and the swallowing sound the sound feature amount.

8. The swallowing evaluation system according to claim 1, further comprising:
an ultrasound probe; and
a microphone incorporated in the ultrasound probe,
wherein the processor when executing the computer-readable instructions is further configured to control the swallowing evaluation system to acquire the swallowing sound by using the microphone.

9. The swallowing evaluation system according to claim 1, further comprising:
an ultrasound probe; and
a microphone that is independent of the ultrasound probe and that is configured to be brought into contact with the pharynx of the subject,
wherein the processor when executing the computer-readable instructions is further configured to control the swallowing evaluation system to acquire the swallowing sound by using the microphone.

10. The swallowing evaluation system according to claim 1,
wherein the swallowing evaluation comprises a hardness of food suitable for the subject to swallow.

11. The swallowing evaluation system according to claim 1, further comprising:
a monitor,
wherein the processor is further configured to control the monitor to display the swallowing evaluation.

12. The swallowing evaluation system according to claim 1, wherein the swallowing sound comprises a waveform representing a change in time of an amplitude of the swallowing sound, and when executing the computer-readable instructions, the processor is configured to control the swallowing evaluation system to determine the image feature amount by comparing image features of the food-like structure in the ultrasound image to image features of food-like structures in pharynges of other subjects, determine the sound feature amount by comparing the waveform to waveforms representing changes in time of amplitudes of swallowing sounds of other subjects.

13. The swallowing evaluation system according to claim 12, wherein when executing the computer-readable instructions the processor is configured to control the swallowing evaluation system to determine the sound feature amount by detecting a peak value of the amplitude of the swallowing sound in an abnormal frequency band as compared to normal swallowing sounds of the other subjects by performing frequency analysis on the swallowing sound.

14. The swallowing evaluation system according to claim 12, wherein when executing the computer-readable instructions the processor is configured to control the swallowing evaluation system to determine the sound feature amount by comparing the changes in time of the amplitudes of the swallowing sounds to the change in time of the amplitude of the swallowing sound and by comparing frequency distributions of the swallowing sounds to a frequency distribution of the swallowing sound.

15. The swallowing evaluation system according to claim 12, wherein when executing the computer-readable instructions the processor is configured to control the swallowing evaluation system to determine an amount of the food-like structure that remains in the epiglottic vallecula and output the first evaluation including the amount.

16. A swallowing evaluation method comprising:
acquiring an ultrasound image in a pharynx of a subject;
acquiring a swallowing sound of the subject;
determining, by inputting the ultrasound image into a neural network, an image feature amount that represents a first degree of abnormality occurring in swallowing of the subject;

determining, by inputting the swallowing sound into the neural network, a sound feature amount that represents a second degree of abnormality occurring in the swallowing of the subject;

determining, based on the first degree of abnormality and the second degree of abnormality, at least one of a first evaluation whether a food-like structure remains in an epiglottic vallecula or a pyriform sinus of the subject and a second evaluation whether dysphagia is suspected in the subject; and outputting a swallowing evaluation of the subject indicating at least one of the first evaluation and the second evaluation, and the neural network being a trained neural network trained to determine the first degree of abnormality using images of pharynges of other subjects and trained to determine the second degree of abnormality using swallowing sounds of the other subjects.

* * * * *